United States Patent [19]
Haas et al.

[11] Patent Number: 6,040,082
[45] Date of Patent: Mar. 21, 2000

[54] VOLUMETRICALLY EFFICIENT BATTERY FOR IMPLANTABLE MEDICAL DEVICES

[75] Inventors: David P. Haas, Brooklyn Park; William G. Howard, Roseville; Ann M. Crespi, Minneapolis; Anthony R. Rorvick, Brooklyn Park; Steven Rockow, Coon Rapids; Andrew J. Ries, Circle Pines, all of Minn.

[73] Assignee: Medtronic, Inc., Minneapolis, Minn.

[21] Appl. No.: 08/903,297

[22] Filed: Jul. 30, 1997

[51] Int. Cl.⁷ ........................................ H01M 4/02
[52] U.S. Cl. ............................ 429/163; 429/131; 429/94
[58] Field of Search .................... 429/163, 164, 429/131, 94

[56] References Cited

U.S. PATENT DOCUMENTS

| | | | |
|---|---|---|---|
| 2,928,888 | 3/1960 | Vogt | 136/6 |
| 3,373,060 | 3/1968 | Gray | 136/100 |
| 3,395,043 | 7/1968 | Shoeld | 136/13 |
| 3,558,356 | 1/1971 | Ropp, Jr. | 136/6 |
| 4,051,304 | 9/1977 | Snook | 429/94 |
| 4,105,832 | 8/1978 | Sugalski | 429/94 |
| 4,332,867 | 6/1982 | Tsuda et al. | 429/94 |
| 4,335,191 | 6/1982 | Peled | 429/94 |
| 4,539,271 | 9/1985 | Crabtree | 429/94 |
| 4,539,274 | 9/1985 | Goebel | 429/94 |
| 4,550,064 | 10/1985 | Yen et al. | 429/94 |
| 4,565,752 | 1/1986 | Goebel et al. | 429/94 |
| 4,565,753 | 1/1986 | Goebel et al. | 429/94 |
| 4,663,247 | 5/1987 | Smilanich et al. | 429/94 |
| 4,664,989 | 5/1987 | Johnson | 429/94 |
| 4,668,320 | 5/1987 | Crabtree | 156/192 |
| 4,767,682 | 8/1988 | Dorogi et al. | 429/94 |
| 4,794,056 | 12/1988 | Pedicini | 429/94 |
| 4,830,940 | 5/1989 | Keister et al. | 429/194 |
| 4,863,815 | 9/1989 | Chang et al. | 429/94 |
| 4,963,445 | 10/1990 | Marple et al. | 429/94 |
| 5,439,760 | 8/1995 | Howard et al. | 429/94 |
| 5,443,925 | 8/1995 | Machida et al. | 429/94 |
| 5,458,993 | 10/1995 | Terao et al. | 429/94 |
| 5,458,997 | 10/1995 | Crespi et al. | 429/219 |
| 5,486,215 | 1/1996 | Kelm et al. | 29/623.1 |
| 5,549,717 | 8/1996 | Takeuchi et al. | 29/623.2 |
| 5,568,558 | 10/1996 | Takeuchi et al. | 429/122 |
| 5,603,737 | 2/1997 | Marincic et al. | 29/23.1 |
| 5,616,429 | 4/1997 | Klementowski | 429/3 |

*Primary Examiner*—Maria Nuzzolillo
*Assistant Examiner*—Monique M. Wills
*Attorney, Agent, or Firm*—Thomas F. Woods; Harold R. Patton

[57] ABSTRACT

A high rate battery having a coiled electrode assembly housed in a case that efficiently utilizes the space available in many implantable medical devices is disclosed. The battery case provides a planar surface opposite an arcuate surface to allow for the close abutting of other components located within the implantable device while also providing for efficient location of the battery within an arcuate edge of the device. The battery cases include at least three planar sides extending between a top and a base of the battery case, wherein the arcuate side is located directly opposite one of the planar sides. The battery case may form a prismatic solid shape with one arcuate surface and five planar surfaces. The batteries may include a coiled electrode assembly including an anode and a cathode; electrolyte; and a case liner containing the electrode assembly. The coiled electrode assembly can have an elliptical cross-section including two arcuate ends, wherein one of the arcuate ends is nested within an arcuate side of the case. The batteries are capable of delivering about 20 joules or more in about 20 seconds or less; and may also be capable of delivering about 20 joules or more at least twice in a period of about 30 seconds. Also included are implantable defibrillator devices incorporating the batteries and methods of manufacturing the batteries including drawing the battery case from metal.

32 Claims, 4 Drawing Sheets

VOLUMETRICALLY EFFICIENT BATTERY FOR IMPLANTABLE MEDICAL DEVICES

FIELD OF THE INVENTION

The present invention relates to the field of batteries for implantable medical devices. More particularly, the present invention relates to volumetrically efficient batteries for implantable medical devices.

BACKGROUND

Implantable medical devices are used to treat patients suffering from a variety of conditions. One example of an implantable medical device is a cardiac defibrillator used to treat patients suffering from ventricular fibrillation, also referred to as tachyarrhythmia. In operation, the defibrillator device constantly monitors the electrical activity of the heart of the patient, detects ventricular fibrillation, and in response to that detection, delivers appropriate shocks to restore normal heart rhythm. Shocks as large as 30–35 joules or more may be needed. The shocks are typically delivered from capacitors capable of providing that energy in a fraction of a second. To provide timely therapy when ventricular fibrillation is detected, the capacitors should be charged with sufficient energy in only a few seconds. As a result, the power source should have a high current rate capability to provide the necessary amount of energy to the capacitors in the limited amount of time, it should also have a low self-discharge rate to extend its useful life, and it should be highly reliable to provide the desired therapy when required. Typically, the power sources used in such devices are lithium electrochemical cells because they provide the desired characteristics identified above.

Implantable defibrillator devices are preferably designed with shapes that are easily accepted by the patient's body and which also minimize patient discomfort. As a result, the corners and edges of the devices are typically designed with generous radii to present a package having smoothly contoured surfaces. It is also desirable to minimize the volume occupied by the devices as well as their mass to further limit patient discomfort. As a result, the devices continue to become thinner, smaller, and lighter.

Known high current rate power sources used in implantable defibrillator devices employ prismatic, six-sided rectangular solid shapes in packaging of the electrode assemblies. Examples of such package shapes can be found in, e.g., U.S. Pat. No. 5,486,215 (Kelm et al.). Typical device layout includes two such power sources centrally located within the device.

Although the use of curved battery cases in implantable devices is known, they are typically found in devices requiring only low current rate discharge such as pacemakers. Batteries with curved cases have been used in connection with the high current rate batteries required for, e.g., implantable defibrillator devices. However, these high current rate batteries used thin, flat layered electrodes that do not package efficiently within curved cases.

Although not admitted as prior art, examples of battery designs can be found in the issued U.S. Patents listed in Table 1 below.

| U.S. Pat. No. | Inventor(s) | Issue Date |
| --- | --- | --- |
| 2,928,888 | Vogt | March 15, 1960 |
| 3,373,060 | Gray | March 12, 1968 |
| 3,395,043 | Schoeld | July 30, 1968 |
| 3,558,358 | Ropp, Jr. | January 26, 1971 |
| 4,051,304 | Snook | September 27, 1977 |
| 4,105,832 | Sugalski | August 8, 1978 |
| 4,332,867 | Tsuda et al. | June 1, 1982 |
| 4,335,191 | Peled | June 15, 1982 |
| 4,539,271 | Crabtree | September 3, 1985 |
| 4,539,274 | Goebel | September 3, 1985 |
| 4,550,064 | Yen et al. | October 29, 1985 |
| 4,565,752 | Goebel et al. | January 21, 1986 |
| 4,565,753 | Goebel et al. | January 21, 1986 |
| 4,663,247 | Smilanich et al. | May 5, 1987 |
| 4,664,989 | Johnson | May 12, 1987 |
| 4,668,320 | Crabtree | May 26, 1987 |
| 4,767,682 | Dorogi et al. | August 30, 1988 |
| 4,794,056 | Pedicini | December 27, 1988 |
| 4,830,940 | Keister et al. | May 16, 1989 |
| 4,863,815 | Chang et al. | September 5, 1989 |
| 4,963,445 | Marple et al. | October 16, 1990 |
| 5,439,760 | Howard et al. | August 8, 1995 |
| 5,443,925 | Machida et al. | August 22, 1995 |
| 5,458,993 | Terao et al. | October 17, 1995 |
| 5,458,997 | Crespi et al. | October 17, 1995 |
| 5,486,215 | Kelm et al. | January 23, 1996 |
| 5,549,717 | Takeuchi et al. | August 27, 1996 |
| 5,569,558 | Takeuchi et al. | October 29, 1996 |
| 5,603,737 | Marincic et al. | February 18, 1997 |
| 5,616,429 | Klementowski | April 1, 1997 |

All patents listed in Table 1 above are hereby incorporated by reference in their respective entireties. As those of ordinary skill in the art will appreciate readily upon reading the Summary of the Invention, Detailed Description of the Preferred Embodiments and Claims set forth below, many of the devices and methods disclosed in the patents of Table 1 may be modified advantageously by using the teachings of the present invention.

SUMMARY OF THE INVENTION

The present invention has certain objects, i.e., various embodiments of the present invention provide solutions to one or more problems existing in the prior art respecting efficient high rate battery case design for implantable medical devices. Among the problems in the prior art is the lack of a high current rate battery case design for use with coiled electrode assemblies that can be: a) efficiently packaged within an arcuate edge of the device housings; and b) provide a planar surface opposite the arcuate surface nested within the arcuate edge of the device housing.

Accordingly, it is an object of the invention to provide a high rate battery having a coiled electrode assembly housed in a case that efficiently utilizes the space available in many implantable medical devices.

It is another object of the invention to provide a high rate battery housed in a case that provides a planar surface opposite an arcuate surface to allow for the close abutting of other components located within the implantable device while also providing for efficient location of the battery within an arcuate edge of the device.

In comparison to known high current rate batteries and battery cases, various embodiments of the present invention may provide one or more of the following advantages: (a) efficient utilization of the volume located within an arcuate edge of an implantable medical device; (b) efficient location of other components in a closely abutting relationship with the planar end of the battery case opposite the arcuate end of the case; (c) ease of manufacturing the case by drawing and other methods; and (d) compatibility with coiled electrode assemblies.

Battery cases in embodiments of the invention may include one or more of the following features: (a) a top; (b) a base located opposite the top; (c) an arcuate side extending between the top and the base; (d) at least three generally planar sides extending between the top and the base of the battery case, wherein the arcuate side is located directly opposite one of the generally planar sides; (e) a battery case wherein the top, base, generally planar sides and arcuate side form a prismatic solid shape with one arcuate surface and five generally planar surfaces; (f) an arcuate side including a generally planar section and at least one arcuate section; (g) an arcuate side including a generally planar section located between two arcuate sections; (h) a case having a generally planar top and generally planar bottom; (i) an open top and a cover for hermetically sealing the top; (j) a cover is welded to the battery case; and (k) a battery case is fabricated from a material selected from the group of stainless steel, aluminum, and titanium.

Batteries in one or more embodiments of the present invention may include one or more of the following features: (a) a coiled electrode assembly including an anode and a cathode; (b) electrolyte; (c) a case liner containing the electrode assembly; (d) a case enclosing the electrode assembly, electrolyte and case liner, the case including a cover, a base located opposite the cover, an arcuate side extending between the cover and the base, and at least three generally planar sides extending between the top and the base of the battery case, wherein the arcuate side is located directly opposite one of the generally planar sides; (e) a battery case forming a prismatic solid shape with one arcuate surface and five generally planar surfaces; (f) a battery case in which the arcuate side includes a generally planar section and at least one arcuate section; (g) a battery case in which the arcuate side includes a generally planar section located between two arcuate sections; (h) a battery in which the cover and the base of the case are generally planar; (i) a hermetically sealed battery case; (j) a battery case having a cover welded to the case; (k) a battery case fabricated from a material selected from the group of stainless steel, aluminum, and titanium; (l) a coiled electrode assembly having an elliptical cross-section including two generally arcuate ends, wherein one of the generally arcuate ends is nested within an arcuate side of the case; (m) a battery capable of delivering about 20 joules or more in about 20 seconds or less; and (n) a battery capable of delivering about 20 joules or more at least twice in a period of about 30 seconds.

Implantable defibrillator devices in one or more embodiments of the present invention may include one or more of the following features: (a) a device housing including at least one arcuate edge; (b) a capacitor located within the device housing; (c) a battery located within the device housing and operatively connected to a capacitor, the battery including a coiled electrode assembly, electrolyte, a case liner; and a hermetically sealed battery case enclosing the electrode assembly, electrolyte and case liner, the case including a cover, a base located opposite the cover, an arcuate side extending between the cover and the base, and at least three generally planar sides extending between the top and the base of the battery case, wherein the arcuate side is located directly opposite one of the generally planar sides, and further wherein the arcuate side of the battery case is nested within one of the arcuate edges of the device housing; (d) a battery case in which the generally planar side of the battery case opposite the arcuate side faces an interior of the device housing; (e) a battery case forming a prismatic solid shape with one arcuate surface and five generally planar surfaces; (f) a coiled electrode assembly having an elliptical cross-section including two generally arcuate ends, wherein one of the generally arcuate ends is nested within an arcuate side of the case; (g) a battery capable of delivering about 20 joules or more in about 20 seconds or less; and (h) a battery capable of delivering about 20 joules or more at least twice in a period of about 30 seconds.

Methods of manufacturing batteries for implantable medical devices according to the present invention may include one or more of the following steps: (a) drawing metal to form a battery case having an open top, a base located opposite the top, an arcuate side extending between the top and the base, and at least three generally planar sides extending between the top and the base of the battery case, wherein the arcuate side is located directly opposite one of the generally planar sides; (b) inserting a case liner into the battery case; (c) inserting a coiled electrode assembly into the case liner; (d) inserting electrolyte into the battery case, (e) attaching a cover to the arcuate side and generally planar sides of a battery case to hermetically seal the open top of the case; (f) drawing a battery case forming a prismatic solid shape with one arcuate surface and five generally planar surfaces; (g) welding a cover to the case; (h) drawing the case from a material selected from the group of stainless steel, aluminum, and titanium; (i) inserting a coiled electrode assembly into a battery case, the coiled electrode assembly having an elliptical cross-section including two generally arcuate ends, wherein one of the generally arcuate ends is nested within an arcuate side of the case; (j) manufacturing a battery capable of delivering about 20 joules or more in about 20 seconds or less; and (k) manufacturing a battery capable of delivering about 20 joules or more at least twice in a period of about 30 seconds.

These and other objects, advantages and features of the inventions will be apparent upon review of the detailed description of preferred embodiments, the drawings, and claims appended hereto.

DETAILED DESCRIPTION OF THE PREFERRED EMBODIMENTS

As used herein, the terms battery or batteries include a single electrochemical cell or cells. Batteries are volumetrically constrained systems in which the components in the case of the battery cannot exceed the available volume of the battery case. Furthermore, the relative amounts of some of the components can be important to provide the desired amount of energy at the desired discharge rates. A discussion of the various considerations in designing the electrodes and the desired volume of electrolyte needed to accompany them in, for example, a lithium/silver vanadium oxide (Li/SVO) battery is discussed in U.S. Pat. No. 5,458,997 (Crespi et al.). Generally, however, the battery must include the electrodes and additional volume for the electrolyte required to provide a functioning battery.

The present invention is particularly directed to high current rate batteries that are capable of charging capacitors with the desired amount of energy, preferably about 20 joules or more, typically about 20 joules to about 70 joules, in the desired amount of time, preferably about 20 seconds or less, more preferably about 10 seconds or less. These values can typically be attained during the useful life of the battery as well as when the battery is new. As a result, the batteries must typically deliver up to about 1 to about 4 amps at about 1.5 to about 2.5 volts, in contrast to low rate batteries that are typically discharged at much lower rates. Furthermore, the preferred batteries must be able to provide these amounts of energy repeatedly separated by about 30 seconds or less, more preferably by about 10 seconds or less.

Figure 1:
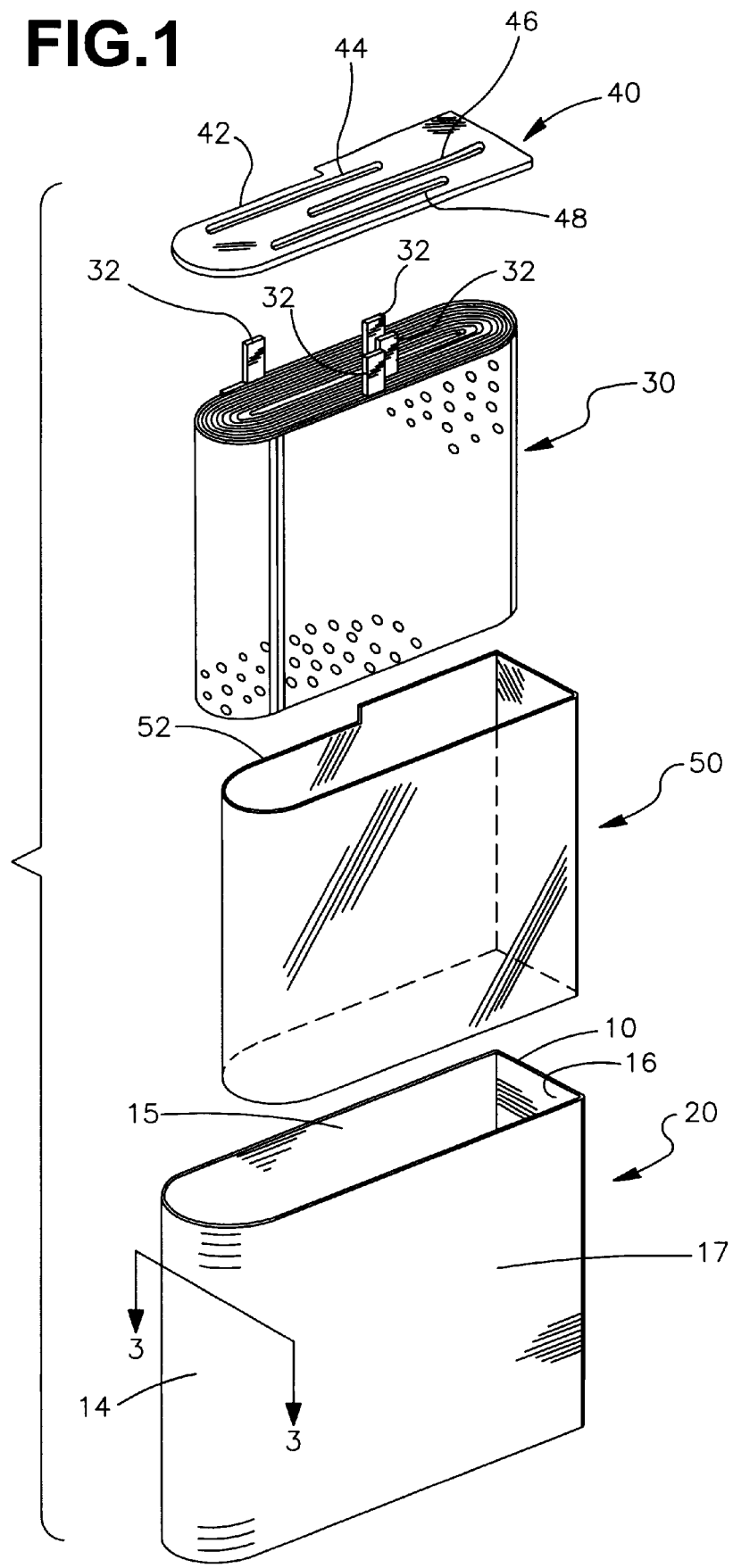
FIG. 1 is an exploded perspective view of a battery case, electrode assembly, case liner and coil insulator in one battery according to the present invention.
Figure 2:
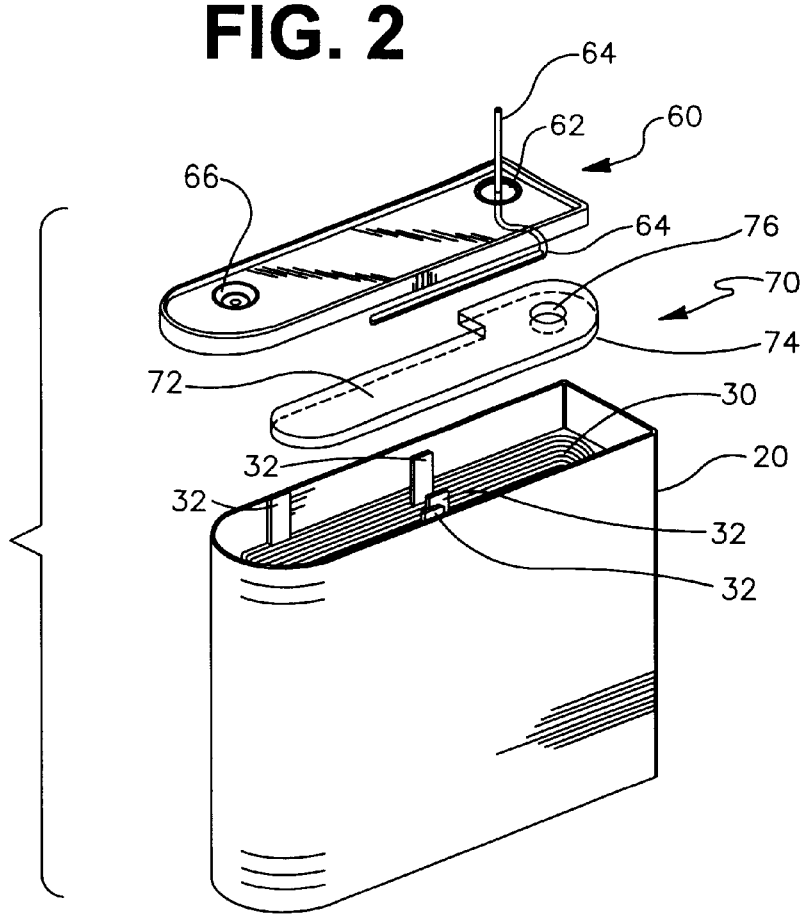
FIG. 2 is an exploded perspective view of the battery of FIG. 1 including the case cover and a headspace insulator.

One preferred battery according to the present invention is depicted in FIGS. 1 and 2 and includes a case 20 and electrode assembly 30. The case 20 is designed to enclose the electrode assembly 30 and be sealed by a case cover 60. The side 14 of the case 20 is preferably generally arcuate in shape while the opposing side 16 of the case 20 is preferably generally planar. This construction provides a number of advantages including the ability to accommodate one of the curved or arcuate ends of a preferred coiled electrode assembly 30. As will be more fully discussed below, the arcuate side 14 can also nest within an arcuate edge of an implantable medical device such as an implantable cardiac defibrillator. When the arcuate side 14 is located within the edge of a device, the planar surface on the opposing side 16 faces inward to assist in the efficient use of space within a device case.

The details regarding construction of the electrode assembly, such as connector tabs, electrode pouches, etc., are secondary to the present invention and will be described generally below with a more complete discussion being found in, e.g., U.S. Pat. No. 5,458,997 (Crespi et al.).

The electrode assembly 30 depicted in FIGS. 1 and 2 is preferably a wound or coiled structure similar to those disclosed in, e.g., U.S. Pat. No. 5,486,215 (Kelm et al.) and U.S. Pat. No. 5,549,717 (Takeuchi et al.). As a result, the electrode assemblies typically exhibit two generally planar sides, bounded by two opposing generally arcuate edges and two opposing generally planar ends. The composition of the electrode assemblies can vary, although one preferred electrode assembly includes a wound core of lithium/silver vanadium oxide (Li/SVO) battery as discussed in, e.g., U.S. Pat. No. 5,458,997 (Crespi et al.). Other battery chemistries are also anticipated, such as those described in U.S. Pat. No. 5,616,429 to Klementowski, with the preferred cores comprising wound electrodes having at least one generally semicircular or arcuate end that is adapted to nest within the arcuate side 14 of the case 20. Such a design provides a volumetrically efficient high current rate battery useful in many different implantable devices.

The electrode assembly 30 preferably includes an anode, a cathode and a porous, electrically non-conductive separator material encapsulating either or both of the anode and cathode. These three components are preferably laminated together and wound to form the electrode assembly 30. The anode portion of the electrode assembly can comprise a number of different materials including an anode active material located on an anode conductor element. Examples of suitable anode active materials include, but are not limited to: alkali metals, materials selected from Group IA of the Periodic Table of Elements, including lithium, sodium, potassium, etc., and their alloys and intermetallic compounds including, e.g., Li—Si, Li—B, and Li—Si—B alloys and intermetallic compounds, insertion or intercalation materials such as carbon, or tin-oxide. Examples of suitable materials for the anode conductor element include, but are not limited to: stainless steel, nickel, titanium, or aluminum.

The cathode portion of the electrode assembly preferably includes a cathode active material located on a cathode current collector that also conducts the flow of electrons between the cathode active material and the cathode terminals of the electrode assembly 30. Examples of materials suitable for use as the cathode active material include, but are not limited to: a metal oxide, a mixed metal oxide, a metal sulfide or carbonaceous compounds, and combinations thereof. Suitable cathode active materials include silver vanadium oxide (SVO), copper vanadium oxide, copper silver vanadium oxide (CSVO), manganese dioxide, titanium disulfide, copper oxide, copper sulfide, iron sulfide, iron disulfide, carbon and fluorinated carbon, and mixtures thereof, including lithiated oxides of metals such as manganese, cobalt, and nickel.

Preferably, the cathode active material comprises a mixed metal oxide formed by chemical addition, reaction or otherwise intimate contact or by thermal spray coating process of various metal sulfides, metal oxides or metal oxide/ elemental metal combinations. The materials thereby produced contain metals and oxides of Groups IB, IIB, IIIB, IVB, VB, VIB, VIIB, and VIII of the Periodic Table of Elements, which includes noble metals and/or their oxide compounds.

The cathode active materials can be provided in a binder material such as a fluoro-resin powder, preferably polytetrafluoroethylene (PTFE) powder that also includes another electrically conductive material such as graphite powder, acetylene black powder and carbon black powder. In some cases, however, no binder or other conductive material is required for the cathode.

The separator material should electrically insulate the anode from the cathode. The material is preferably wettable by the cell electrolyte, sufficiently porous to allow the electrolyte to flow through the separator material, and maintain physical and chemical integrity within the cell during operation. Examples of suitable separator materials include, but are not limited to: polyethylenetetrafluoroethylene, ceramics, non-woven glass, glass fiber material, polypropylene, and polyethylene.

Insertion of the electrode assembly 30 into case 20 is also depicted in FIG. 2. As best seen in FIG. 1, however, a coil insulator 40 is placed on the electrode assembly 30. The coil insulator 40 includes a notch 42 to accommodate one of the connectors tabs 32 on the electrode assembly 30 and slits 44, 46 and 48 to accommodate other connector tabs 32.

The electrode assembly 30 is also preferably inserted into an electrically non-conductive case liner 50. The case liner 50 preferably extends at its top edge above the edge of the electrode assembly 30 to overlap with other electrically non-conductive elements. If the case liner 50 does extend above the electrode assembly 30, it preferably includes a notch 52 on one side to allow for the connection between one set of the connector tabs 32 to the case 20. The electrode assembly 30, coil insulator 40 and case liner 50 are then preferably inserted into the case 20.

FIG. 2 also depicts the case cover 60 and a headspace insulator 70 along with the case 20 and the electrode assembly 30. One preferred case cover 60 includes a feedthrough 62 through which feedthrough pin 64 is inserted. The feedthrough pin 64 is preferably conductively insulated from the cover 60 by any suitable material where it passes through the cover 60. The feedthrough pin 64 preferably is bent to align itself with the desired connector tabs 32 extending from the electrode assembly 30. The preferred case cover 60 also includes a fill port 66 that is used to introduce an appropriate electrolyte solution after which the fill port 66 is hermetically sealed by any suitable method.

The headspace insulator 70 is preferably located below the case cover 60 and above the coil insulator 40, i.e., in the headspace above the coiled electrode assembly 30 and below the cover 60 The preferred headspace insulator 70 includes a raised surface 72 supported above the electrode assembly 30 by a sidewall or skirt 74 that preferably extends about the periphery of the headspace insulator 70. A well 76 is preferably formed in the raised surface 72 where the feedthrough pin 64 is inserted through the headspace insulator 72. The well 76 in the headspace insulator 72 is preferably adapted to receive the structure surrounding the feedthrough 62 formed in the cover 60 (which typically extends below the lower surface of the cover 60 by some distance). The headspace insulator 70 is provided to electrically insulate the feedthrough pin 64 from the case 20 and the case cover 60. The headspace insulator 70 forms a chamber in connection with the upper surface of the coil insulator 40 that isolates the feedthrough pin 64 and the connector tabs 32 to which is attached. Additional insulation in the form of tubing or a coating (not shown) around or on the feedthrough pin 64 may also be included to further insure electrical isolation of the feedthrough pin 64.

Although one specific coil insulator, headspace insulator, cover, and electrode assembly with connector tabs is depicted in FIGS. 1 and 2, it should be understood that that any suitable apparatus could be substituted for those depicted as long as the function of insulating the tabs and the feedthrough pin is accomplished.

The case 20 and case cover 60 are preferably constructed of an electrically conductive material including, but not limited to: stainless steel, aluminum, titanium, etc. It is preferred that the case 20 be manufactured by drawing the metal into the desired shape, although other methods of construction are also envisioned. It is also preferable that the case 20 and case cover 60 be made of materials that can be easily joined and hermetically sealed by, e.g., welding. The feedthrough pin 64 should also be electrically conductive. Examples of suitable materials for the feedthrough pin 64 include, but are not limited to: niobium and molybdenum. The coil insulator 40, case liner 50 and headspace insulator 70 are preferably made of an electrically non-conductive material including, but not limited to: a polyolefin polymer and a fluoropolymer (e.g., PETFE and PECTFE).

After the electrode assembly 30 is located within case 20 and the cover 60 has been sealed in place, the battery can be filled with the electrolyte required to activate the battery. Examples of suitable electrolytes include any suitable nonaqueous, ionically conductive electrolyte to serve as a medium for migration of ions between the anode and cathode during the electrochemical reactions of the cell. Typically the electrolyte includes an inorganic, ionically conductive salt dissolved in a nonaqueous solvent, more preferably the electrolyte includes an ionizable alkali metal salt dissolved in a mixture of aprotic organic solvents including a low viscosity solvent and a high permittivity solvent.

It should be noted that the present invention is not directed to the composition of the electrode assembly. Rather, the present invention provides a battery case and methods of manufacturing and using the same that efficiently packages a coiled electrode assembly in a case having an arcuate side.

The battery case 20 depicted in FIGS. 1 and 2 includes a top 10 and base 12 connected by four sides 14, 15, 16 and 17. Sides 15 and 17 are generally opposed to each other and sides 14 and 16 are also generally opposed to each other. The top 10 is typically open as shown to allow for the insertion of an electrode assembly 30 and any other desired components. Although top 10 is open in the depicted case 20, it will be understood that any portion of the battery case 20 could be open in place of top 10.

Figure 3:
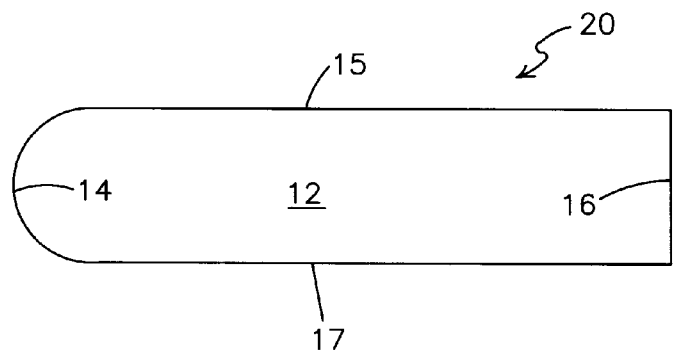
FIG. 3 is a cross-section al view of the battery case of FIG. 1, taken along line 3—3 in FIG. 1.

A cross-sectional view of the case 20 is depicted in FIG. 3 (with the electrode assembly 30 removed). The side 14 of the case 20 is preferably generally arcuate in shape while the opposing side 16 of the case 20 is preferably generally planar. This construction provides a number of advantages including the ability to accommodate one of the curved or arcuate ends of a preferred coiled electrode assembly 30. As will be more fully discussed below, the arcuate side 14 can also nest within an arcuate edge of an implantable medical device such as an implantable cardiac defibrillator. When the arcuate side 14 is located within the edge of a device, the planar surface on the opposing side 16 faces inward to assist in the efficient use of space within a device case.

FIG. 3 also illustrates that the opposing sides 15 and 17 of the case 20 are preferably generally parallel to each other and are also preferably generally planar. Likewise, the base 12 of the case 20 is also preferably generally planar. The base 12 is preferably attached to the sides 14, 15, 16, and 17 at ninety degree angles. In other words, the case 20 can be described as including five generally planar surfaces (top 10, base 12, and sides 15, 16, 17) arranged in the shape of prismatic rectangular solid in which one side 14 of the solid is an arcuate surface as opposed to a generally planar surface.

One important advantage of this design is that, as compared to a completely prismatic six-sided case (as disclosed in, e.g., U.S. Pat. No. 5,603,737 to Marincic et al.) the present invention provides a battery having increased volumetric efficiency. That increase in volumetric efficiency is provided as a result of a better, more conformal fit between one arcuate or rounded end of the coiled electrode assembly 30 and the arcuate side 14 of the battery case 20. The space at the opposite end of the battery case 20 that is not occupied by the electrode assembly 30 can be advantageously used as a portion of the reservoir needed to contain the electrolyte solution.

One measure of volumetric efficiency of a battery can be stated in terms of ampere hours per cubic centimeter. In one example of a battery according to the present invention in which surface area of the electrodes is 90 square centimeters, the volume of a battery 10 including one arcuate side designed to enclose the electrode assembly and associated electrolyte etc. is 8.6 cubic centimeters and yields a battery 10 having a volumetric efficiency of 182 milliampere-hours per cubic centimeter. To enclose an electrode assembly having the same dimensions in a battery case in which all of the six sides were generally planar would result in battery having a volume of about 9.0 cubic centimeters, resulting in a volumetric efficiency of about 174 milliampere-hours per cubic centimeter.

The shape of the arcuate side 14 of the case 20 is depicted as generally semicircular, but it will be understood that a side having any suitable arcuate shape that connects the base 12 and two opposing sides 15 and 17 could be substituted. Examples of some suitable alternate arcuate shapes for the arcuate side 14 of the case 20 include elliptical, parabolic, and other arcuate shapes.

Figure 4:
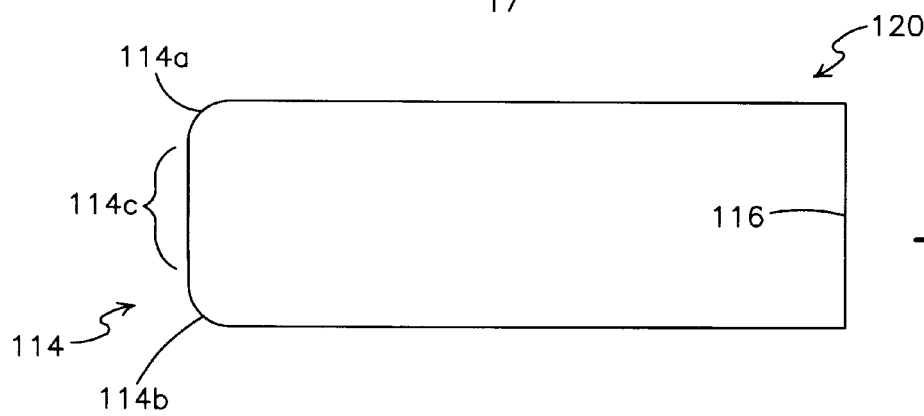
FIG. 4 is a cross-sectional view of one alternative battery case design.

In addition to a pure arcuate side, i.e., a side in which all of the surfaces are arcuate in shape, the arcuate side of the case could be provided as the composite of two arcuate sections between which one or more planar surfaces are located. One example of an alternate case 120 having an arcuate side 114 with a composite shape is depicted in FIG. 4. The two opposing sides 115 and 117 of the case 120 are each connected to an arcuate section 114*a*/114*b* between which generally planar section 114*c* is interposed. In a further alternative, the central section 114*c* could be another arcuate section having a different radius of curvature or profile than the two sections 114*a*/114*b* on either side.

The shape of the arcuate side 114 of the battery case 120 can be distinguished from a battery case having a prismatic six-sided rectangular solid shape in which generally planar sides are joined along their edges by a radiused joint (drawn or otherwise formed). One distinguishing feature is that the arcuate surface or surfaces that form the arcuate side of the battery case preferably generally conform to the arcuate shape of a coiled electrode assembly to be placed in the battery case. Radiused edges used in connecting the planar sides of a battery case would typically have a radius of curvature that is too small to generally conform to the shape of a wound electrode assembly. It may be preferred that the ratio of the radius of curvature of the arcuate side of the battery case to the radius of curvature of the arcuate end of a wound electrode assembly be about 0.5:1 to about 2:1, more preferably about 0.75:1 to about 1.5:1, and even more preferably about 1:1. In one embodiment similar to that depicted in FIG. 4, the radius of curvature of the arcuate sections 114*a*/114*b* is about 0.12 inches (3 millimeters) or more.

Figure 5:
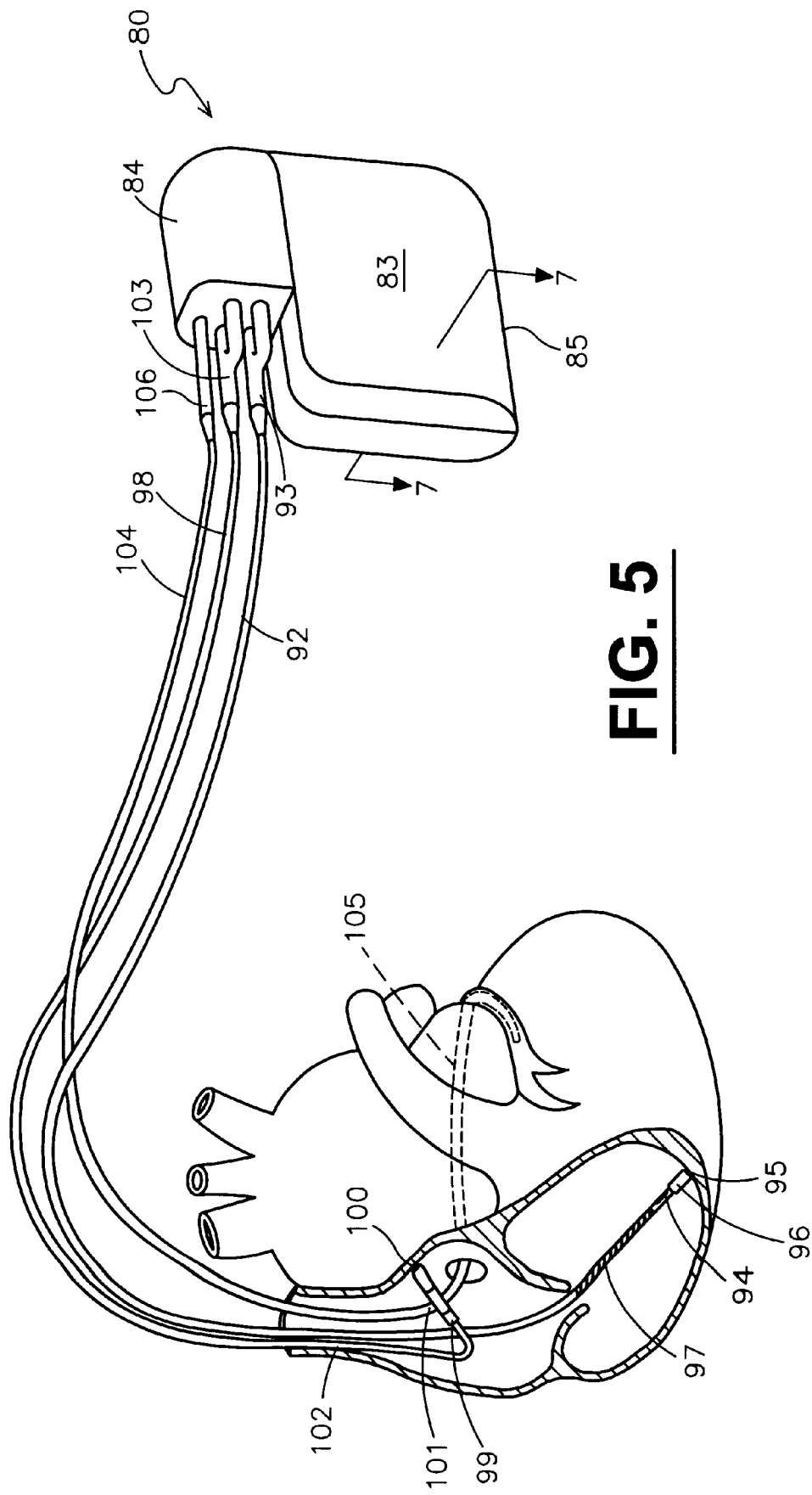
FIG. 5 is a schematic representation of an implantable medical device including a battery having a battery case according to the present invention.

The batteries and battery cases according to the present invention can be used in a variety of implantable medical devices. FIG. 5 illustrates one defibrillator 80 and lead set 90 in which the defibrillator includes a battery with an arcuate side according to the present invention. The ventricular lead includes an elongated lead body 92 carrying three concentric coiled conductors separated from each other by tubular insulative sheaths. A ring electrode 94, extendible helix electrode 95 retractably mounted within an insulative electrode head 96, and an elongated defibrillation coil electrode 97 are located adjacent the distal end of the lead body 92. Each of the electrodes 94 and 95 is coupled to one of the coiled conductors within the lead body 92. Electrodes 94 and 95 can be used for cardiac pacing and for sensing ventricular depolarization. At the proximal end of the lead body 92 is a bifurcated connector 93 that carries three electrical connectors, each coupled to one of the coiled conductors in the lead body 92. The defibrillation coil electrode 97 may be fabricated from platinum, platinum alloy or other materials known to be usable in implantable defibrillation electrodes and may be, e.g., about 5 centimeters in length.

The atrial/SVC lead includes an elongated insulative lead body 98 carrying three concentric coiled conductors separated from each other by tubular insulative sheaths corresponding to the structure of the ventricular lead body 92. Located adjacent the J-shaped distal end of the lead body 98 are a ring electrode 99 and an extendible helix electrode 100, mounted retractably within an insulative electrode head 101. Each of the electrodes 99 and 100 is coupled to one of the coiled conductors within the lead body 98. Electrodes 99 and 100 are used for atrial pacing and for sensing atrial depolarizations. An elongated coil electrode 102 is provided proximal to the ring electrode 99 and coupled to the third conductor within the lead body 98. The atrial/SVC electrode is preferably about 10 centimeters or more in length and is configured to extend from the SVC toward the tricuspid valve. In one preferred embodiment, approximately 5 centimeters of the right atrium/SVC electrode was located in the right atrium, with the remaining 5 centimeters located in the SVC. At the proximal end of the lead body 98 is a bifurcated connector 103 that carries three electrical connectors, each coupled to one of the coiled conductors in the lead body 98.

The coronary sinus lead includes an elongated insulative lead body 104 carrying one coiled conductor coupled to a defibrillation electrode 105. The defibrillation electrode 105, illustrated in broken outline in FIG. 5, is located within the coronary sinus and great vein of the heart. At the proximal end of the lead body 104 is a connector plug 106 that carries an electrical connector coupled to the coiled conductor in the lead body 104. The coronary sinus/great vein electrode 105 may be about 5 centimeters in length.

The implantable pacemaker/cardioverter/defibrillator 80 is shown with the lead connector assemblies 93, 103, and 106 inserted into the connector block 84 mounted on housing 82. Optionally, insulation of the outward facing portion of the housing 82 of the pacemaker/cardioverter/defibrillator 80 may be provided using a plastic coating, e.g., parylene or silicone rubber as is currently employed in some unipolar cardiac pacemakers. However, the outward facing portion may instead be left uninsulated, or some other division between the insulated and uninsulated portions may be employed. The uninsulated portion of the housing 82 optionally serves as a subcutaneous defibrillation electrode, used to defibrillate either the atria or ventricles. Other lead configurations and electrode locations may of course be substituted for the lead set illustrated. For example, atrial defibrillation and sensing electrodes might be added to either the coronary sinus lead or the right ventricular lead instead of being located on a separate atrial lead, thereby allowing for a two-lead system.

The batteries used in pacemaker/cardioverter/defibrillator 80 must be reliable because of the critical functions they perform, which is especially true for defibrillators used to prevent death from lethal arrhythmia. Defibrillators often operate in combination with a pacemaker. During operation, defibrillators continuously monitor a patient's heart rate. Thus, it is important that such implantable device batteries be able to deliver the desired pulsing current with a minimal voltage drop during the pulse. As a result, it is important that the batteries do not exhibit a high increase in internal resistance over discharge time of the battery.

As illustrated in FIG. 5, the housing 82 includes two spaced-apart opposing sides 83 that are connected about their periphery by edges 85. At least some of the edges 85 are preferably arcuate in shape to limit the presence of sharp corners or edges that may cause or increase patient discomfort. The exact dimensions of the device housing 82 are variable as is the exact shape of the edges 85.

Figure 6:
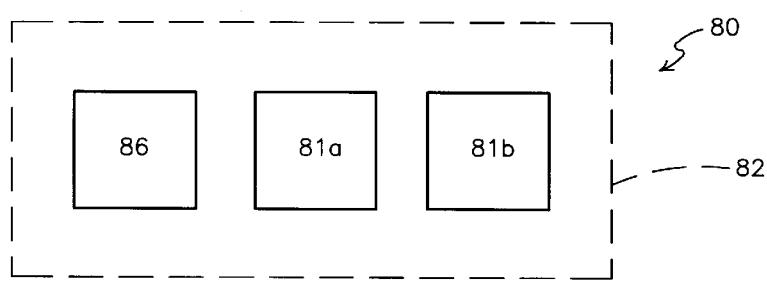
FIG. 6 is a schematic block diagram of the components included in the implantable medical device of FIG. 5.

Similar to the battery design described above, the device 80 is also a volumetrically constrained system in which the components in the device housing 82 cannot exceed the available volume. The components of such a device 80 are schematically depicted in FIG. 6 and include, within the housing 82, a power source 86 (typically one or more batteries) and other components 81a and 81b required to both monitor heart rhythm and provide the desired therapy when required.

Figure 7:
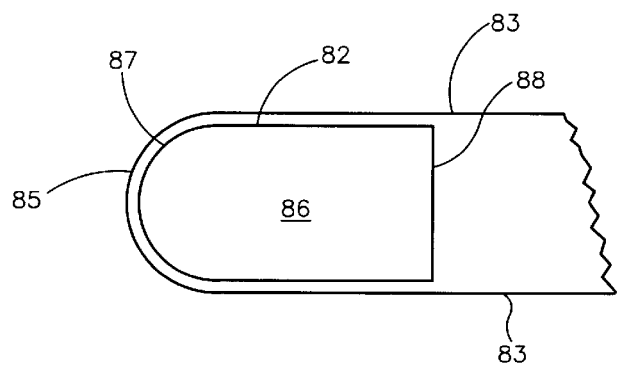
FIG. 7 is a partial cross-sectional view of the implantable medical device of FIG. 5, taken along line 7—7 in FIG. 5.

FIG. 7 is an enlarged partial cross-sectional view of the device 80 in which a battery 86 including a case having an arcuate side 87 nested within one of the arcuate edges 85 of the device housing 82. By providing a battery 86 that efficiently fits within the arcuate edge 85 of the housing 82, the overall volume within the housing 82 of the device 80 may be more efficiently utilized.

In addition to nesting the arcuate side 87 of the battery 86 in the arcuate edge 85 of the housing 82, the side 88 of the battery 86 opposite the arcuate side 87 is preferably generally planar as shown in FIG. 7. This generally planar surface is advantageous in that other components within the device 80 will typically include at least one planar surface that can be placed in an abutting relationship with the planar side 88 of the battery 86. As a result, the other components within the device 80 may be more efficiently packaged within the device housing 82.

The preceding specific embodiments are illustrative of the practice of the invention. It is to be understood, therefore, that other expedients known to those skilled in the art or disclosed herein, may be employed without departing from the invention or the scope of the appended claims. For example, the present invention is not limited to battery cases including ends formed with arcuate edges having constant radii of curvature, but could include battery cases with edges having varying radii of curvature or sections having different radii of curvature. The present invention is also not limited to battery cases for implantable defibrillator devices per se, but may also find further application in the design of battery cases for other implantable medical devices such as pacemakers, infusion pumps, etc. The present invention further includes within its scope methods of making and using the battery cases described above.

What is claimed is:

1. A prismatic battery case for a high current rate electrochemical cell for an implantable medical device, comprising:
   a top;
   a base located opposite the top;
   an arcuate side extending between the top and the base;
   three planar sides extending between the top and the base of the battery case, wherein the an arcuate side is located directly opposite one of the planar sides.

2. A battery case according to claim 1, wherein the top, the base, the generally planar sides and the planar arcuate side form a prismatic shape.

3. A battery case according to claim 1, wherein the arcuate side comprises a planar section in combination with at least one arcuate section.

4. A battery case according to claim 1, wherein the arcuate side comprises a planar section disposed between two arcuate sections.

5. A battery case according to claim 1, wherein the top and the bottom of the battery case are planar.

6. A battery case according to claim 5, wherein the top forms an open end and further wherein the battery case comprises a cover for hermetically sealing the top of the case.

7. A battery case according to claim 6, wherein the cover is welded to the battery case.

8. A battery case according to claim 1, wherein the battery case is fabricated from a material selected from the group of stainless steel, aluminum, and titanium.

9. A high current rate battery for an implantable medical device, comprising:
   a coiled electrode assembly including an anode and a cathode;
   an electrolyte;
   a case liner containing the electrode assembly; and
   a prismatic case enclosing the electrode assembly and within which the electrode assembly, the electrolyte and the case liner are disposed, the case comprising a cover, a base located opposite the cover, the arcuate side extending between the cover and the base, and all the three planar sides extending between the top and the base of the battery case, wherein the arcuate side is located directly opposite one of the planar sides.

10. A battery according to claim 9, wherein the arcuate side comprises a planar section and at least one arcuate section.

11. A battery according to claim 9, wherein the arcuate side comprises a planar section disposed between two arcuate sections.

12. A battery according to claim 9, wherein the cover and the base are planar.

13. A battery according to claim 12, wherein the case is hermetically sealed.

14. A battery according to claim 13, wherein the cover is welded to the case.

15. A battery according to claim 9, wherein the case is fabricated from a material selected from the group of stainless steel, aluminum, and titanium.

16. A battery according to claim 9, wherein the coiled electrode assembly comprises an elliptical cross-section having two arcuate ends, and further wherein one of the substantially convex ends nests within the arcuate side of the case.

17. A battery according to claim 9, wherein the battery is capable of delivering about 20 joules or more in about 20 seconds or less.

18. A battery according to claim 17, wherein the battery is capable of delivering about 20 joules or more at least twice in a period of about 30 seconds.

19. A high rate battery for an implantable medical device, comprising:
   an hermetically sealed prismatic case comprising a cover, a base located opposite the cover, a arcuate side extending between the cover and the base, and three planar sides extending between the top and the base of the battery case, the arcuate side being located opposite one of the planar sides;
   a case liner disposed within the case;
   an electrolyte disposed within the case; and
   a coiled electrode assembly disposed within the case liner, the electrode assembly including an anode and a cathode, wherein the electrode assembly comprises an elliptical cross-section having two arcuate ends, and further wherein one of the arcuate ends of the electrode assembly nests within the arcuate side of the case.

20. An implantable defibrillator device, comprising:
   a device housing comprising at least one arcuate edge;
   a capacitor disposed within the device housing, and
   a battery disposed within the device housing and operatively connected to the capacitor, the battery comprising:

a coiled electrode assembly;
an electrolyte;
a case liner, and
an hermetically sealed battery case within which the electrode assembly, the electrolyte and the case liner are disposed, the case comprising a cover, a base located opposite the cover, a arcuate side extending between the cover and the base, and three planar sides extending between the top and the base of the battery case, wherein the arcuate side is located directly opposite one of the planar sides, and further wherein the arcuate side of the battery case nests within one of the arcuate edges of the device housing.

21. A device according to claim 20, wherein the planar side of the battery case opposite the arcuate side faces an interior portion of the device housing.

22. A device according to claim 20, wherein the cover, the base, the planar sides and the arcuate side of the battery case form a prismatic shape.

23. A device according to claim 20, wherein the coiled electrode assembly comprises an elliptical cross-section having two arcuate ends, and further wherein one of the arcuate ends nests within the substantially convex side of the case.

24. A device according to claim 20, wherein the battery is capable of delivering about 20 joules or more in about 20 seconds or less.

25. A device according to claim 24, wherein the battery is capable of delivering about 20 joules or more at least twice in a period of about 30 seconds.

26. A method of manufacturing a battery for an implantable medical device, comprising:

drawing metal to form a battery case having an open end, a base located opposite the open end, a arcuate side extending between the open end and the base, and three planar sides extending between the open end and the base, wherein the arcuate side is located directly opposite one of the planar sides;

inserting a case liner into the battery case;

inserting a coiled electrode assembly into the case liner;

placing an electrolyte inside the battery case;

placing a cover over the open end of the case, and hermetically sealing the cover to the case.

27. A method according to claim 26, wherein the cover, the base, the planar sides and the arcuate side of the case form a prismatic shape.

28. A method according to claim 26, wherein the cover is welded to the case.

29. A method according to claim 26, wherein the case is drawn from a material selected from the group of stainless steel, aluminum, and titanium.

30. A method according to claim 26, wherein the coiled electrode assembly comprises an elliptical cross-section having two arcuate ends, and further wherein one of the arcuate ends nested within the substantially convex side of the case.

31. A method according to claim 26, wherein the battery is capable of delivering about 20 joules or more in about 20 seconds or less.

32. A method according to claim 31, wherein the battery is capable of delivering about 20 joules or more at least twice in a period of about 30 seconds.

* * * * *